（12) United States Patent
Sasayama

(10) Patent No.: US 7,576,841 B2
(45) Date of Patent: Aug. 18, 2009

(54) PHOTOMETRIC APPARATUS

(75) Inventor: Tomoki Sasayama, Kyoto (JP)

(73) Assignee: Shimadzu Corporation, Kyoto-Fu (JP)

( * ) Notice: Subject to any disclaimer, the term of this patent is extended or adjusted under 35 U.S.C. 154(b) by 340 days.

(21) Appl. No.: 11/723,290

(22) Filed: Mar. 19, 2007

(65) Prior Publication Data

US 2007/0279616 A1 Dec. 6, 2007

(30) Foreign Application Priority Data

Jun. 2, 2006 (JP) ............... 2006-154685

(51) Int. Cl.
G01N 21/00 (2006.01)
G01N 21/33 (2006.01)
(52) U.S. Cl. .................. 356/51; 356/319; 356/326; 250/373

(58) Field of Classification Search ............... 356/51, 356/319; 250/372, 373
See application file for complete search history.

(56) References Cited

FOREIGN PATENT DOCUMENTS

JP         11-211566 A        8/1999

Primary Examiner—F. L Evans
(74) Attorney, Agent, or Firm—Sughrue Mion, PLLC

(57) ABSTRACT

A photometric apparatus which includes a cover that houses a UV light source and a photodetector, the cover hermetically sealing an entire light path extending from the light source to the photodetector therewithin; device for replacing an internal atmosphere of the cover with nitrogen gas; and a window plate unit which is adapted to be readily attached to and detached from a partition wall between a light source chamber and a spectral chamber located in a subsequent stage thereof. The window plate unit blocks gaseous communication between the light source chamber and the spectral chamber while allowing measurement light to be transmitted therethrough.

2 Claims, 5 Drawing Sheets

Deep UV measurement

Non-deep UV measurement

PHOTOMETRIC APPARATUS

BACKGROUND OF THE INVENTION

1. Field of the Invention

The present invention relates to a photometric apparatus, such as a spectrophotometric apparatus, and more particularly to a photometric apparatus having an ultraviolet (UV) light source.

2. Description of the Related Art

There has been known a spectrophotometric apparatus which is equipped with a UV light source, such as a deuterium lamp, and designed to spectrally disperse light emitted from the light source by a wavelength dispersive element, and detect light components of respective wavelengths after undergoing interaction with a sample to obtain an intensity distribution on a per wavelength basis so as to analyze the sample quantitatively and/or qualitatively, wherein oxygen which exhibits an absorption peak in a deep UV region is eliminated from a light path to allow measurements to be accurately performed even on a shorter wavelength side of the deep UV region. This type of spectrophotometric apparatus is provided with a mechanism for supplying replacement gas (i.e., inert gas, such as nitrogen, helium or argon gas), to replace an internal atmosphere of the apparatus with the gas (hereinafter referred to as "gas replacement operation"), and/or a mechanism for providing a vacuum to an internal space of the apparatus using a vacuum pump or the like (hereinafter referred to as "vacuuming operation"). These mechanisms are activated when a measurement in the deep UV region (hereinafter referred to as "deep UV measurement") is performed, so as to purge oxygen from the internal space of the apparatus, as disclosed in Japanese Patent Laid-Open Publication No. 11-211566 (paragraphs [0022], [0023]).

Generally, UV light reacts with oxygen in the atmosphere to generate ozone. This ozone has adverse effects on rubber materials and various other materials in the long and medium terms, as is commonly known. A photometric apparatus equipped with a UV light source also involves ozone generation around the light source, and some internal parts of the photometric apparatus, such as parts of an optical-element driving mechanism, are likely to be adversely affected by the ozone. Ozone-induced corrosion in the internal parts will contribute to deterioration in durability and reliability of the apparatus.

Particularly, in the type of photometric apparatus designed to perform the deep UV measurement, the internal space including the light path is kept in a hermetically sealed state relative to an outside environment to efficiently carry out the gas replacement or vacuuming operation, which is required for the deep UV measurement. Thus, ozone gas generated around the light source is likely to fill the inner space of the apparatus during measurements in UV wavelength regions other than the deep UV region (these measurements will hereinafter be referred to as "non-deep UV measurements"). This accelerates corrosion in the internal parts, even though this problem can be avoided as long as the deep UV measurement is performed, because oxygen causing ozone generation is purged through the gas replacement or vacuuming operation during deep UV measurement. While this photometric apparatus may be designed to extend, to the non-deep UV measurements, the vacuuming or gas (e.g., nitrogen gas) replacement operation for the deep UV measurement, measurement or running costs will be extremely increased although the internal parts can be protected from the ozone-induced corrosion. Thus, in terms of economical efficiency, it is undesirable to operate the vacuum pump or supply the replacement gas when there is no need for the deep UV measurement, only for the purpose of diluting or eliminating ozone.

SUMMARY OF THE INVENTION

In view of the above circumstances, it is an object of the present invention to provide a photometric apparatus capable of effectively preventing the occurrence of corrosion in internal parts thereof due to ozone gas originated around a UV light source, and minimally suppressing an introduction of replacement gas or an operation of a vacuum pump to reduce running costs.

In order to achieve the above object, the present invention provides a photometric apparatus including: a frame member which houses a light source for generating measurement light of an ultraviolet region and a photodetector for detecting the measurement light after undergoing interaction with a sample, and hermetically seals an entire light path extending from the light source to the photodetector therewithin; and air purge means for purging air from an internal space of the frame member. The photometric apparatus includes a spatial-isolation member designed to be installed in the internal space detachably or displaceably in such a manner as to allow the measurement light to be transmitted therethrough, and block gaseous communication between a space defined as a part of the internal space of the frame member to contain the light source therein, and the remaining internal space of said frame member.

In the above photometric apparatus of the present invention, gaseous communication between the space for containing the ultraviolet (UV) light source therein and the remaining internal space of the frame member can be blocked by the spatial-isolation member. This makes it possible to preclude ozone gas generated around the UV light source from getting into the remaining internal space of the frame member, such as a spectral chamber, so as to prevent the occurrence of corrosion in internal parts of the photometric apparatus.

Further, the spatial-isolation member is designed to be installed the internal space detachably or displaceably. Thus, an operator can readily attach/detach or displace the spatial-isolation member without using a tool or the like, to selectively arrange the spatial-isolation member on the light path or remove the spatial-isolation member from the light path, according to need. For example, in a deep UV measurement, it is undesirable that a light-transmittable member, such as a lens or a window plate, is arranged on the light path. Thus, the deep UV measurement may be performed without arranging the spatial-isolation member on the light path, under the condition that air purge means, such as a vacuum pump or replacement-gas supply means, is operated. Further, measurements in UV wavelength regions other than the deep UV region (i.e., non-deep UV measurements) may be performed without operating the air purge means, under the condition that the spatial-isolation member is arranged on the light path. In this manner, the operation of the air purge means, such as a vacuum pump or replacement gas supply means, can be limitedly carried out only during the deep UV measurement, so as to contribute to reduction in running costs.

BRIEF DESCRIPTION OF THE DRAWINGS

FIGS. 2A and 2B illustrate gaseous communication around a light source chamber in the spectrophotometric apparatus according to the embodiment, wherein FIG. 2A shows a state of gaseous communication during a deep UV measurement, and FIG. 2B shows a state of gaseous communication during non-deep UV measurements.

FIGS. 3A and 3B illustrate the structure of a window plate unit in the spectrophotometric apparatus according to the embodiment, wherein FIG. 3A is a front view of the window plate unit, and FIG. 3B is a sectional view of the window plate unit in a state after being attached to a partition wall.

FIGS. 4A and 4B illustrate an operation of attaching the window plate unit, wherein FIG. 4A is an enlarged front view of the window plate unit in a state after a pin head is inserted into a guide hole, and FIG. 4B is a sectional view of the window plate unit in this state.

FIGS. 5A and 5B illustrate the operation of attaching the window plate unit, wherein FIG. 5A is an enlarged front view of the window plate unit in a state after a window-plate holder is pushed downwardly, and FIG. 5B is a sectional view of the window plate unit in this state.

DETAILED DESCRIPTION OF THE EXEMPLARY EMBODIMENT

Figure 1:
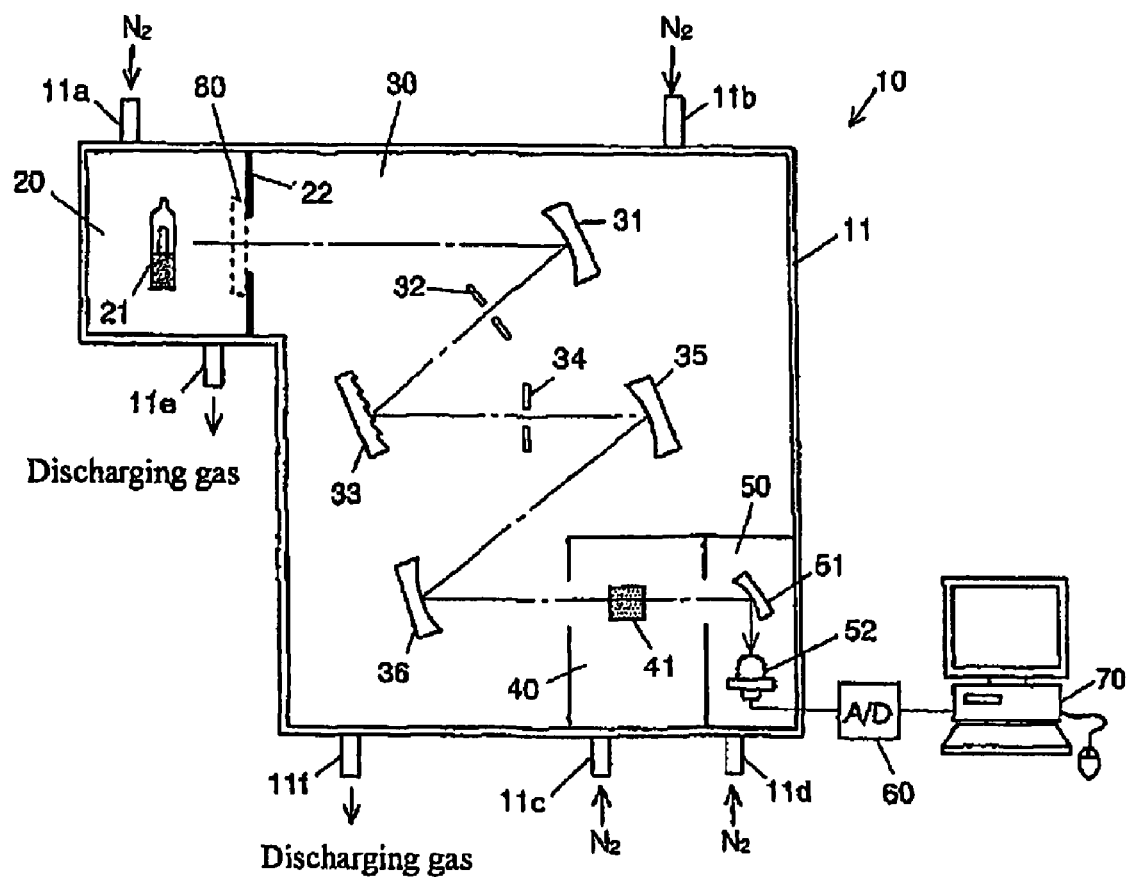
FIG. 1 is schematic diagram showing a spectrophotometric apparatus according to one embodiment of the present invention.

The present invention will now be described based on an exemplary embodiment thereof. FIG. 1 is schematic diagram showing a spectrophotometric apparatus according to the embodiment of the present invention.

The spectrophotometric apparatus 10 according to this embodiment includes a light source chamber 20 containing therein an ultraviolet (UV) light source 21 composed of a deuterium lamp, a spectral chamber 30 which contains therein a diffraction grating 33 and others, a sample chamber 40 adapted to allow a sample 41 to be set therein, and a detector chamber 50 containing therein a photodetector 52. The spectrophotometric apparatus 10 includes a cover 11 which generally defines the light source chamber 20, the spectral chamber 30, the sample chamber 40 and the detector chamber 50, in such a manner that an entire light path formed in these chambers 20, 30, 40, 50 is hermetically sealed from an outside environment to allow a gas replacement operation to be effectively performed. The cover 11 is provided with four gas inlet ports 11a, 11b, 11c, 11d for introducing nitrogen gas serving as replacement gas, into the respective chambers 20, 30, 40, 50, and two gas outlet ports 11e, 11f for discharging gas residing in the chambers 20, 30, 40, 50. Further, the cover 11 is provided with a first partition wall separating between the light source chamber 20 and the spectral chamber 30, a second partition wall separating the spectral chamber 30 and the sample chamber 40, and a third partition wall separating the sample chamber 40 and the detector chamber 50. Each of the first to third partition walls is formed with an opening for allowing measurement light to pass therethrough. That is, gas can freely move between the adjacent chambers.

Measurement light emitted from the UV light source 21 gets into the spectral chamber 30, and enters the diffraction grating 33 through a mirror 31 and a slit 32. The diffraction grating 33 is designed to be rotated about an axis perpendicular to the drawing sheet of FIG. 1 so as to have a wavelength selection function. Monochromatic light components as the measurement light wavelength-dispersed by the diffraction grating 33 are led into the sample chamber 40, and directed toward the sample 41. The measurement light after being transmitted through the sample 41 gets into the detector chamber 50, and enters the photodetector 52 through a mirror 51. In the photodetector 52, the measurement light is converted to an electrical signal representing respective intensities of the monochromatic light components. The spectrophotometric apparatus may be designed to allow each of the light source and the photodetector to be appropriately replaced with a suitable one for each wavelength region to be selected, i.e., measured. The electrical signal output from the photodetector 52 is converted to digital data by an A/D conversion section 60. The digital data is recorded as spectral intensity data in a control computer, such as a personal computer, and then a qualitative or quantitative analysis of the sample will be performed based on the spectral intensity data.

Figure 2A:
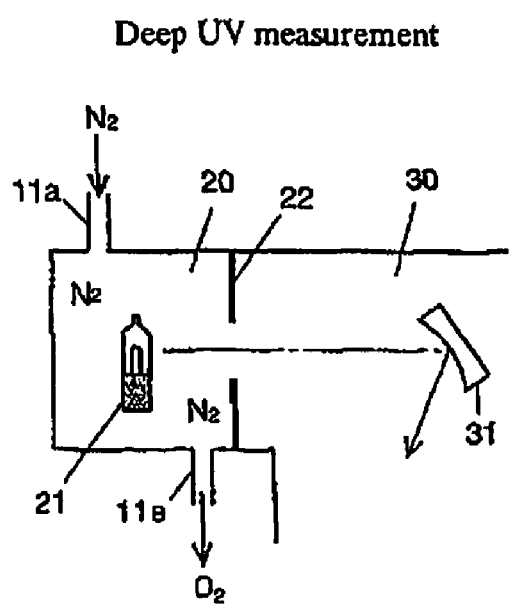

In the spectrophotometric apparatus according to this embodiment, a measurement in the deep UV region (i.e., deep UV measurement) is performed under the condition that nitrogen gas is introduced from the inlet ports 11a, 11b, 11c, 11d into an internal space of the apparatus to purge and replace air on the light path with the nitrogen gas so as to eliminate oxygen capable of absorbing deep UV light. Further, the spectrophotometric apparatus is designed to allow any light-transmittable member, such as a lens or a window plate, to be not arranged on the light path during the deep UV measurement, so as to more stably obtain a measurement result even on a shorter wavelength side of the deep UV region. Thus, gas can freely move between the light source chamber 20 and the spectral chamber 30 and between the adjacent chambers located in subsequent stages. Even in this state, adverse effects of ozone on internal parts of the apparatus can be fully avoided, because nitrogen gas is introduced into the internal space during the deep UV measurement to purge ozone-inducing oxygen from the apparatus (see FIG. 2A), and ozone which is likely to be generated from residual oxygen can also be diluted or purged by the nitrogen gas before its concentration reaches an unacceptably high level.

In non-deep UV measurements having no need for data in the deep UV region, it is not necessary to carry out the above operation of introducing nitrogen gas. Thus, the non-deep UV measurements are performed under a presence of air in the internal space of the apparatus, in the same manner as that in conventional spectrophotometric apparatuses. In order to change the measurement condition in the above manner, in advance of the non-deep UV measurements, a window plate unit 80 is detachably attached to the first partition wall 22 to cover the opening of the first partition wall 22 so as to block gaseous communication between the light source chamber 20 and the spectral chamber 30.

The window plate unit 80 includes a window plate 81 which is transparent to the measurement light, and a window-plate holder 82 adapted to hold the window plate 81. The window plate unit 80 is detached during the deep UV measurement, and therefore there is no need for selecting a material of the window plate 81 in consideration of absorption in the deep UV region. Preferably, the window plate 81 is made of a material having no absorption peak in the UV wavelength regions other than the deep UV region. For example, the suitable material may include quartz. The window plate unit 80 also includes an O-ring 84 which is mounted on a rear surface (a surface to be in opposed relation to the first partition wall 22 when the window plate unit 80 is attached to the first partition wall 22) of the window-plate holder 82 in such a manner as to surround an outer periphery of the window plate 81. Thus, in a state after the window plate unit 80 is attached, the O-ring 84 hermetically seals between the light source chamber 20 and the spectral chamber 30.

The first partition wall 22 between the light source chamber 20 and the spectral chamber 30 is provided with a window-plate-unit mounting pin 23 at a position in a vicinity of the measurement-light transmitting opening thereof, and the window-plate holder 82 is formed with a guide hole 83 at a position corresponding to the pin 23. The pin 23 has a shank or anchor portion 23b, and a head 23a with an outer diameter greater than that of the anchor portion 23b. The guide hole 83 has a large-bore portion 83a having an inner diameter greater than the outer diameter of the head 23a, and a slit-shaped elongate-hole portion 83b formed to extend upwardly from the large-bore portion 83a and have a width which is less than the outer diameter of the head 23a and slightly greater than the outer diameter of the anchor portion 23b. In this specification, a vertical (i.e., upward/downward) direction is defined on the basis of a state after the detachable window plate unit 80 is attached to the first partition wall 22.

Figure 2B:
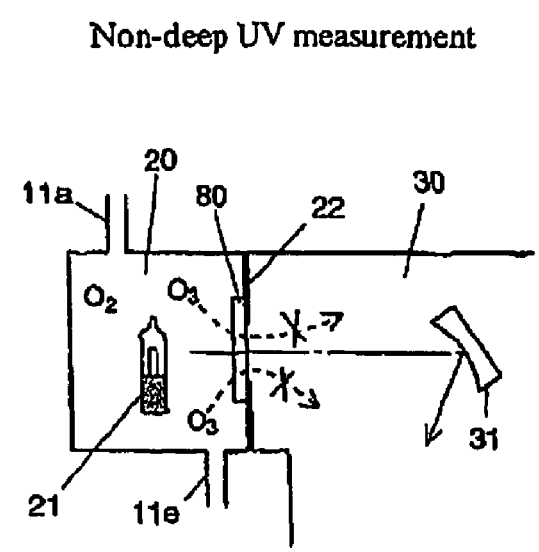
Figure 3A:
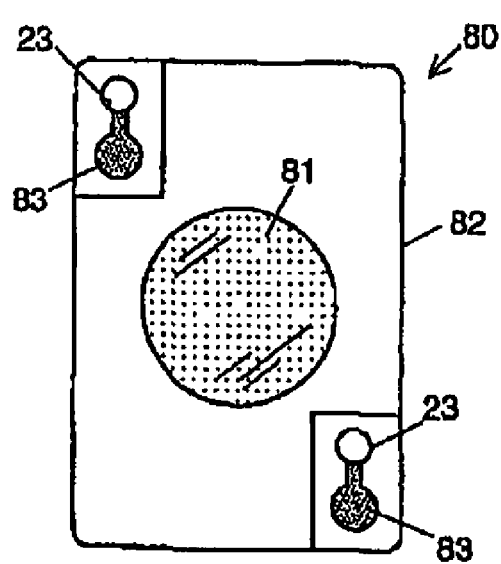
Figure 3B:
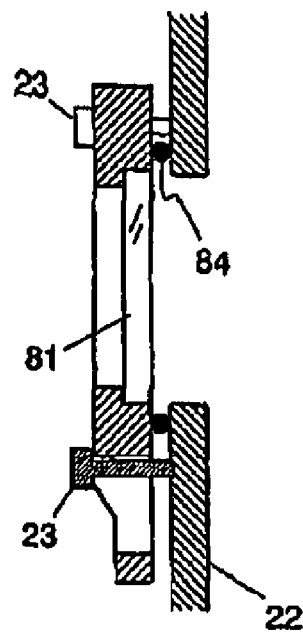
Figures 4A, 4B:
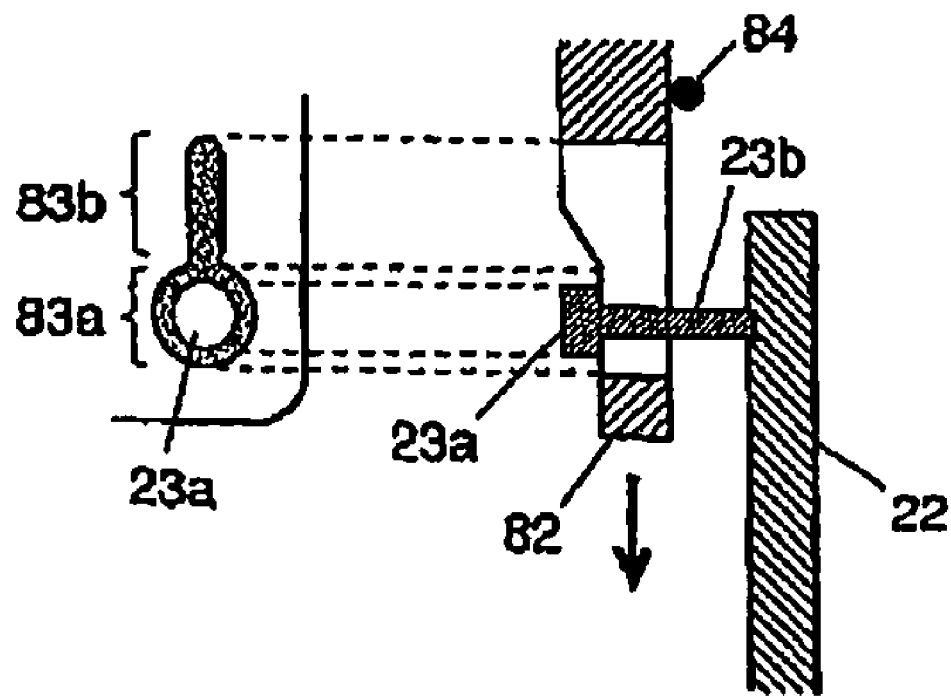
Figures 5A, 5B:
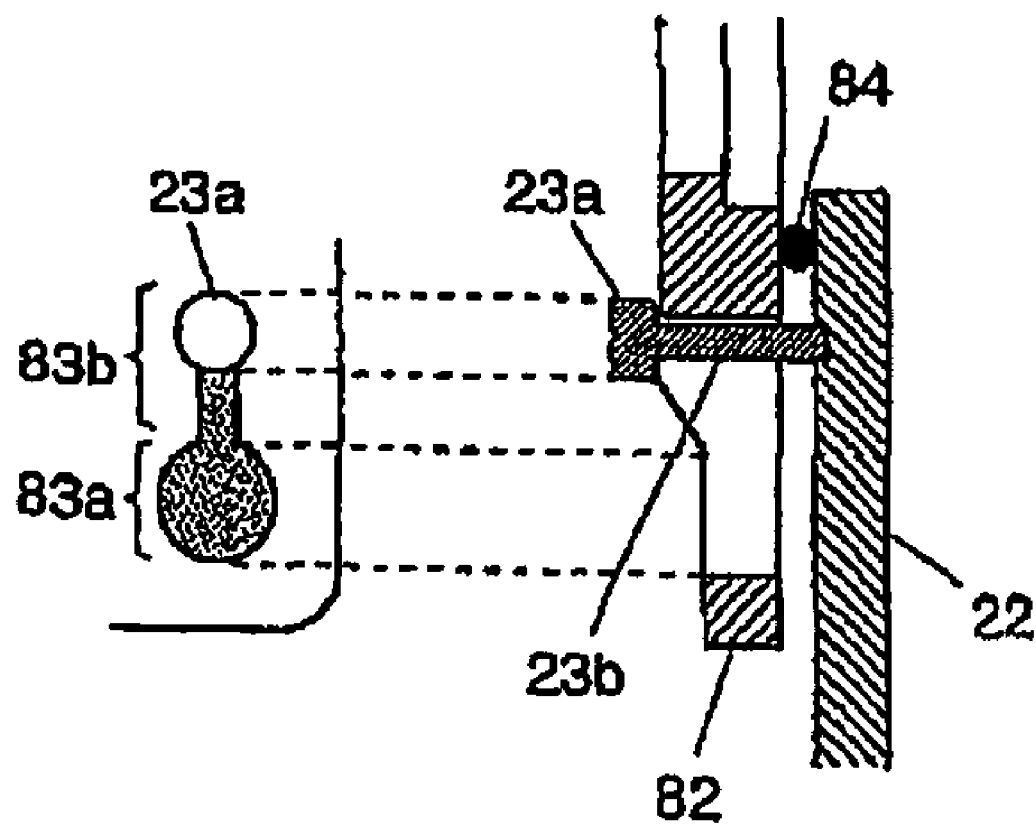

In an operation of attaching the window plate 80 to the first partition wall 22 in advance of the non-deep UV measurements, the pin 23 is firstly inserted into the large-bore portion 83a (see FIGS. 4A and 4B), and then the wind-plate holder 82 is pushed downwardly to move the anchor portion 23b of the pin 23 up to an upper end of the elongate-hole portion 83b to achieve engagement between the pin 23 and the window-plate holder 82 (see FIGS. 5A and 5B). As shown in FIGS. 4B and 5B, the window-plate holder 82 is formed to have a thickness which decreases around the large-bore portion 83a and increases toward the upper end of the elongate-hole portion 83b. Thus, through the operation of pushing the wind-plate holder 82 downwardly after inserting the pin 23 into the guide hole 83, the window plate 80 will be moved toward the first partition wall 22. Thus, the O-ring 84 mounted on the rear surface of the window-plate holder 82 is brought into close contact with the periphery of the opening of the first partition wall 22 to hermetically seal a gap between the window-plate holder 82 and the first partition wall 22 so as to preclude gaseous communication between the light source chamber 20 and the spectral chamber 30 (see FIG. 2B). This makes it possible to prevent the occurrence of an undesirable situation where ozone gas generated around the UV light source 21 fills the inner spaces of the other chambers during the non-deep UV measurements and accelerate corrosion in internal parts of the apparatus.

Even in the state after the window plate unit 80 is attached to the first partition wall 22, UV light passes through the window plate 8 and reaches the spectral chamber 30 and the subsequent chambers 40, 50, and thereby ozone can be generated in the inner spaces of these chambers in some degree. However, as compared with a total amount of UV light emitted from the light source 21, an amount of UV light reaching the spectral chamber 30 and the subsequent chambers 40, 50 is small in view of the optical arrangement. Further, in the non-deep UV measurements, after the measurement light is transmitted through the window plate 81, light components of relatively short wavelength ranges in the transmitted UV light will be cut off. Thus, an amount of ozone to be generated in the spectral chamber 30 and the subsequent chambers 40, 50 will be significantly reduced. Therefore, without carrying out the gas replacement operation using nitrogen gas, an ozone concentration in an entire light path extending from the spectral chamber 30 to the detector 50 can be sufficiently lowered only by restricting gaseous communication between the light source chamber 20 and each of the spectral chamber 30 and the subsequent chambers 40, 50. It is understood that an internal part susceptible to ozone is not arranged in the light source chamber 20. For example, the O-ring 84 of the window plate unit may be made of an ozone-proof material, such as silicon rubber.

As mentioned above, in the spectrophotometric apparatus according to this embodiment, in advance of the non-deep UV measurements having no need for data in the deep UV region, the window plate unit can be installed in the apparatus to prevent ozone generated in the light source chamber from getting into the subsequent chambers. Thus, the operation of introducing nitrogen gas can be limitedly carried out only during the deep UV measurement, so as to facilitate reduction in running costs. Further, the window plate unit is designed to be readily attachable and detachable. Thus, in advance of the deep UV measurement, the window plate unit can be readily detached to prevent the occurrence of optical attenuation due to transmission through the window plate so as to accurately perform the measurement.

Although the present invention has been described based on a exemplary embodiment thereof, this description is not meant to be construed in a limiting sense, but various changes and modifications may be made therein without departing from the spirit and scope thereof as set forth in appended claims. For example, a spatial-isolation member in the present invention is not limited to the structure as shown in the above embodiment, but may have any other suitable structure capable of being attached/detached or displaced by an operator. Specifically, the spatial-isolation member may be designed to be selectively opened and closed, like a hatch, by fixing one edge of the wind-plate holder to the first partition wall through a hinge or the like, or may be designed to be slidingly moved vertically or laterally along a guide rail or the like which is fixed to the first partition wall, so that the window plate can be selectively displaced on and out of the optical path.

What is claimed is:

1. A photometric apparatus including:
   a frame member which houses a light source for generating ultraviolet measurement light and a photodetector for detecting the measurement light after undergoing interaction with a sample, said frame member hermetically sealing an entire light path extending from said light source to said photodetector therewithin; and
   air purge means for purging air from an internal space of said frame member; and
   a spatial-isolation member designed to be installed in said internal space detachably or displaceably in such a manner as to allow the measurement light to be transmitted therethrough, and to block gaseous communication between a space, defined as a part of the internal space of said frame member that includes said light source therein, and a remaining internal space of said frame member.

2. The photometric apparatus as defined in claim 1, wherein said spatial-isolation member is detachably attached to a partition wall disposed between said space that includes said light source therein and said remaining internal space, said spatial-isolation member comprising:
   a) a window plate which is transparent to the measurement light, and configured to cover an opening formed in said partition wall;
   b) a window-plate holder for holding said window plate;
   c) a mounting device that detachably fixes said window-plate holder to said partition wall;
   d) a seal that hermetically seals said window-plate holder to said partition wall.

* * * * *